(12) United States Patent
Nubling et al.

(10) Patent No.: US 6,967,652 B1
(45) Date of Patent: Nov. 22, 2005

(54) METHOD AND APPARATUS FOR DISPLAYING PHYSIOLOGICAL PATIENT DATA

(75) Inventors: Achim Michael Nubling, Denzlingen (DE); Thomas Friedrich Eberle, Emmendingen (DE); Rolf Band, Gottenheim (DE)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 339 days.

(21) Appl. No.: 09/711,691

(22) Filed: Nov. 13, 2000

(51) Int. Cl.$^7$ .............................................. G06T 11/20
(52) U.S. Cl. .................. 345/440; 345/440.1; 345/441; 345/442
(58) Field of Search ............................ 345/440, 440.1, 345/441, 442

(56) References Cited

U.S. PATENT DOCUMENTS

| | | | |
|---|---|---|---|
| 3,638,066 A | 1/1972 | Paine et al. | |
| 4,175,264 A * | 11/1979 | Schiff | 345/24 |
| 5,109,862 A | 5/1992 | Kelen et al. | |
| 5,121,470 A * | 6/1992 | Trautman | 345/440 |
| 5,361,776 A * | 11/1994 | Samuelson et al. | 600/547 |
| 5,622,178 A | 4/1997 | Gilham | |
| 5,827,195 A | 10/1998 | Lander | |
| 5,830,150 A | 11/1998 | Palmer et al. | |
| 5,846,206 A | 12/1998 | Bader | |
| 5,956,013 A | 9/1999 | Raj et al. | |
| 5,967,994 A | 10/1999 | Wang | |
| 6,001,060 A | 12/1999 | Churchill et al. | |
| 6,047,206 A * | 4/2000 | Albrecht et al. | 600/509 |
| 6,409,659 B1 * | 6/2002 | Warner et al. | 600/300 |
| 6,558,325 B1 * | 5/2003 | Pang et al. | 600/443 |

FOREIGN PATENT DOCUMENTS

| | | |
|---|---|---|
| FR | 2414235 | 8/1979 |
| WO | WO 94/10905 | 5/1994 |

\* cited by examiner

*Primary Examiner*—Matthew C. Bella
*Assistant Examiner*—Tam Tran
(74) *Attorney, Agent, or Firm*—Andrus, Sceales, Starke & Sawall, LLP

(57) ABSTRACT

A method and apparatus for acquiring and displaying physiological patient data from a cyclic physiological waveform in a three dimensional representation wherein the amplitude of the data is represented in color and displayed.

23 Claims, 5 Drawing Sheets

METHOD AND APPARATUS FOR DISPLAYING PHYSIOLOGICAL PATIENT DATA

The invention relates to a method and apparatus for displaying physiological patient data from a cyclic physiological waveform, and particularly, to a method and apparatus for displaying physiological patient data from a cyclic physiological waveform in a colorized three-dimensional representation.

Medical patient monitors are typically employed by physicians and other health care providers to monitor the physiological data of patients in operating rooms, intensive care units and emergency rooms, and for conducting long-term trend monitoring such as Holter monitoring or stress testing.

An array of sensors (also commonly called transducers) are typically connected to the patient to acquire the various physiological data. These data are then displayed on the screen of a monitor either in graphical or numerical form. These data may also be recorded or displayed on analog or digital strip chart recorders, spreadsheets and plotting programs.

In prior patient monitoring systems, and particularly in Holter and stress testing systems, it was found to be advantageous to take a series of successive periods of physiological patient data and cascade the periods in a quasi-three-dimensional display format to render visually obvious the abnormalities attendant to certain physiological conditions. However, this kind of data presentation can become cluttered if too many waveform samples are displayed at any one time. Moreover, some users of the equipment find such a display presentation visually unappealing, notwithstanding the clinical importance of the display technique.

SUMMARY OF THE INVENTION

Accordingly, the invention provides a method of displaying physiological and/or pathological patient data from a cyclic physiological or pathological waveform. Hereinafter, the terms "physiological data" or "physiological patient data" shall be broadly defined as including pathological data, or any other type of patient information that is capable of being displayed using the invention. The method includes acquiring the physiological patient data, storing the physiological patient data in a waveform array, and displaying the physiological patient data on a display with a color component that is capable of plotting a three dimensional representation of the data. Although it is not possible to display a three dimensional graph on a two dimensional display, the display represents a three dimensional graph by stacking two dimensional waveforms offset of each other to denote perspective or depth. This method of displaying allows the operator to view a two dimensional image that represents a three dimensional image. Hereinafter, the "X coordinate" shall denote the respective position of each data point with respect to time, the "Y coordinate" shall denote the amplitude of each data point, and the "Z coordinate" shall denote the respective temporal alignment, or offset position of each successive waveform. In one form of the invention, the step of displaying the physiological patient data includes parsing the waveform array into a series of successive waveforms such that each successive waveform is plotted in a temporal alignment to allow easy detection of long term trends in physiological data, parsing each successive waveform into a series of successive data points such that each data point is plotted at a representative X coordinate, Y coordinate, and Z coordinate, and assigning a color (which may be a shade of gray in the case of a black and white monitor or a variation in intensity in the case of a monochrome monitor) according to the amplitude of the data point. The waveform array may be physiological data that represents individual physiological cycles such as heart beats, or the waveform array may be data that has been aggregated in some fashion such as averaging or filtering, or reduction to a median complex.

The invention also provides an apparatus for acquiring and displaying physiological patient data. The apparatus includes a sensor or a transducer for acquiring physiological patient data from a patient, a processor for receiving the physiological patient data, storing the physiological data in a waveform array, and for generating a waveform display on a display. The processor parses the waveform array into a series of successive waveforms, and assigns each successive waveform a respective Z coordinate. The processor also divides each waveform into a series of successive data points and assigns each data point a respective X coordinate. Next, the processor assigns a color (which may be a shade of gray in the case of a black and white monitor, or a variation in intensity in the case of a monochrome monitor) according to the Y coordinate of the data point and plots the data point on the display monitor so that the pixel at the respective coordinate is energized using that color.

It is an advantage of the invention to provide a method and apparatus of displaying amplitude differences of physiological patient data using a gray scale or color display three-dimensional representation.

Other features and advantages of the invention are set forth in the following drawings, detailed description and claims.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENTS

Figure 1:
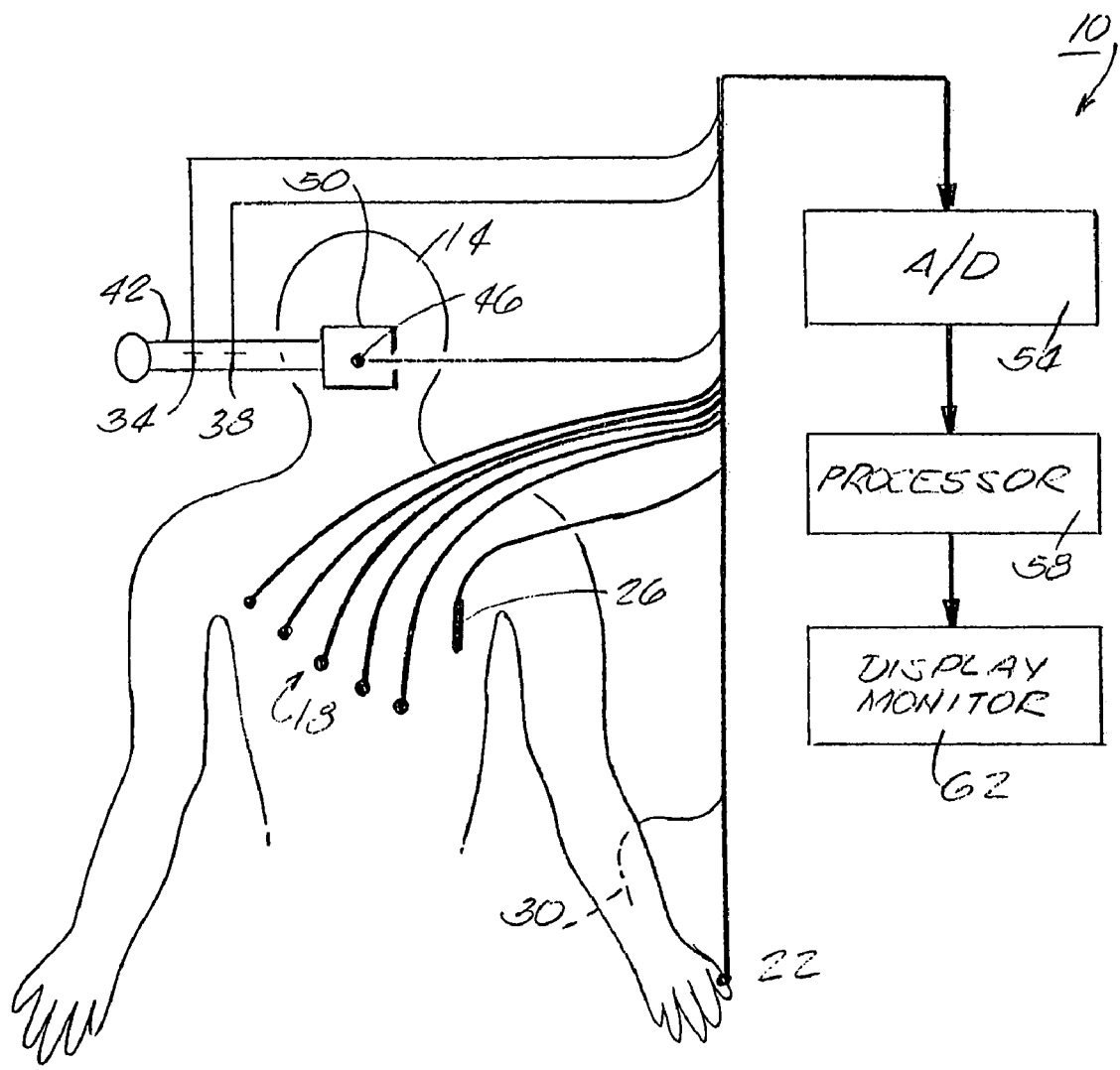
FIG. 1 is a block diagram illustrating a patient monitoring system according to the invention.

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "compris- FIG. 1 illustrates the patient monitoring system 10 of the invention. The patient monitoring system 10 acquires and displays physiological patient data from a cyclic physiological waveform. While the monitoring system 10 can be used in connection with any kind of clinical environment, in the preferred embodiment, the monitoring system 10 is for conducting long-term trend monitoring such as in Holter monitoring or stress testing. Monitoring system 10 is coupled to the patient 14 by an array of sensors or transducers which may include, for example, electrodes 18 mounted on the patient's chest for determining electrocardiogram and heart rate, an oximetry sensor 22 mounted on the patient's finger for measuring hemoglobin oxygen saturation, a catheter 26 for measuring hemoglobin oxygen saturation in the vena cava in the central venus pressure, an arterial canula 30 for measuring arterial systolic and diastolic pressures, flow meter 34 and a pressure sensor 38 in the endotrachial tube 42 for measuring trachial gas flow, and airway pressure, respectively, and sensors 46 in the patient's mask 50 for measuring the volume percentage of oxygen and $CO_2$ in the patient's mouth. Hereinafter, the terms "sensor" and "transducer" will be used synonymously, and each term will be defined as including the subject matter of the other term.

The signals derived from the sensors are converted from analog form to digital form by the analog to digital converter 54 and are then provided to a processor 58 that prepares the data for display on display monitor 62. The monitor is a conventional computer-style display monitor having a generally rectangular cathode ray tube or CRT (not shown). The CRT includes a plurality of pixels. As is known in the art, each pixel is capable of being energized electronically so that the pixel emits light visible to the user of the monitoring system.

In the preferred form of the invention, the display monitor 12 is capable of displaying full color pixels, i.e., the display monitor is an RGB color monitor capable of displaying 256 colors or more. In other embodiments however, a black and white display capable of showing black, white and a plurality of gray shades (preferably no less than 64) in between is acceptable. The term "color" as used in this application is used to indicate either true color or shades of gray as described above unless the context indicates otherwise. Also, while any physiological patient data may be displayed in the format of the preferred embodiment, the invention will be discussed in the context of displaying long-term electrocardiogram ("ECG") data. As is commonly known in the art, the ECG data is subjected to (input 2) a software program that averages or "incrementally" averages the data to produce a series of median waveform complexes. These median waveform complexes are often separated and visually stacked on a display to provide an easily viewable representation of a significant amount of ECG data.

Figure 2:
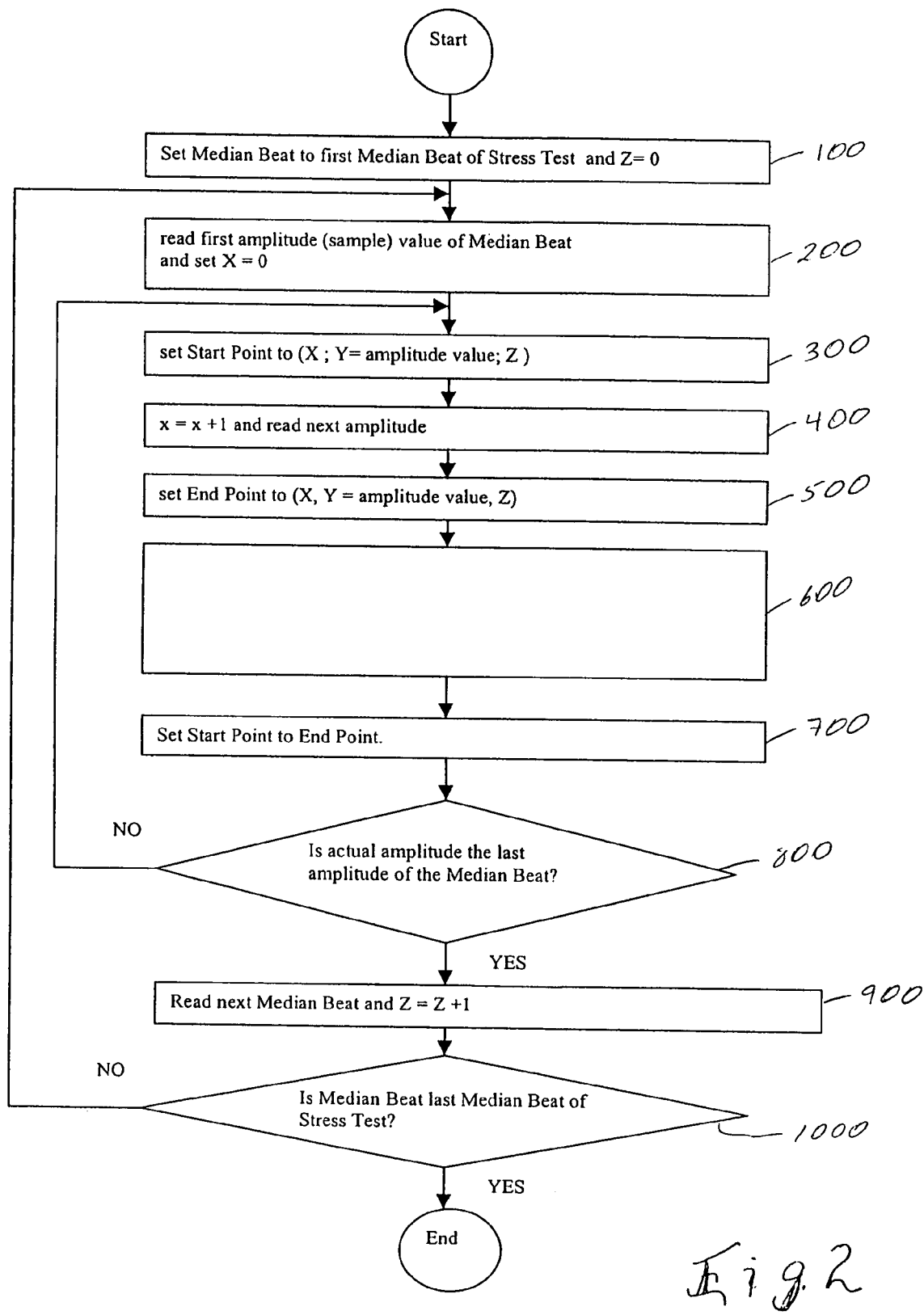
FIG. 2 is a flow chart illustrating the method of the invention.

FIG. 2 illustrates a flowchart of a method embodying the invention. The waveforms (or in the case of the preferred embodiment, the median waveform complexes) are stored in a waveform array, are processed by the software routine stored in the processor 58, and are displayed on the display monitor 62 in a quasi-three-dimensional color display. The display includes x, y, and z axes where the x-axis coordinate represents the data point of a given median waveform complex, the y-axis coordinate represents the amplitude of the data point, and the z-axis coordinate represents the median waveform complex.

Figure 8:
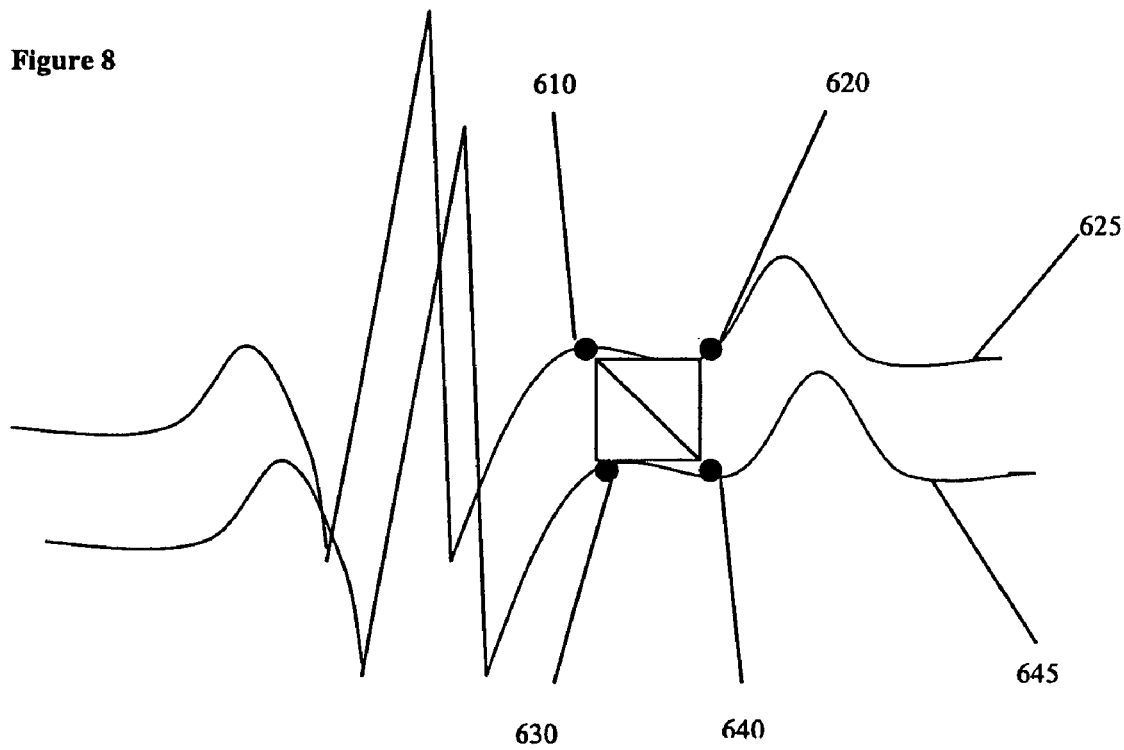
FIG. 8 is a schematic representation of the method of coloring the display as shown in FIGS. 3(a) and 3(b).

The processor sets the current waveform count to the first waveform in the waveform array, i.e., the processor initializes the z coordinate 100 (Z=0). The processor then initializes the x coordinate counter (X=0) and reads the amplitude of the first data sample 200. The processor then sets a variable (START POINT) to be the present data point (which at the beginning of the process is X=0; Y=present amplitude value; and Z=0) 300. The software then increments the x coordinate value by one in order to read the next data point and then reads the amplitude of that data point 400. Next the software sets the variable (END POINT) to be the incremented xyz coordinate 500. The processor then draws two triangles between the data points and colors the triangles based on the amplitude color-code 600. While any color code can be used, including gray scale and variations in intensity, the color code of the preferred embodiment is illustrated in FIGS. 3(a) and 3(b) in the lower left hand corner of these figures. As shown in FIGS. 3(a) and 3(b), the color-code establishes a different color for amplitude values ranging between negative 0.5 millivolts and positive 0.5 millivolts. The software program draws the triangles by establishing a quadrilateral around the START POINT and END POINT variables, 610 and 620, respectively, of the present median beat 625, and the START POINT and END POINT variables 630 and 640, respectively, of the previous median beat 645 with the same X-coordinate value as the START POINT and END POINT variables 610 and 620 (see FIG. 8). Next, the software dissects the quadrilateral by establishing a line between the START POINT variable 610 and the END POINT variable 640. The color is then set for the display based on the amplitude value of the START POINT variable 610 using the amplitude color-code. The software then changes the START POINT variable to END POINT variable 700, and determines whether the data point is the last data point of the present median beat or median complex 800. If not, the software program returns to set the START POINT variable 300 and repeats process steps 300 through 800 until the last data point of the median beat is analyzed. At that point, the software program increments the z coordinate to read the next median beat 900. The software program then determines alternatively whether the median beat is the last median beat of the stress test or whether the data point being analyzed is the last data point of the data set 1000. If not, the software program repeats the process starting at act 200. If so, the software process ends.

In the preferred form of the invention, the color scheme of the monitoring system 10 is fully configurable. That is, the user can select any color to represent a given amplitude. Alternatively, the monitoring system 10 is programmed to provide the user with a set of manufacturer defined color schemes. In the preferred form of the invention, there is graphical and numerical information generated on the display to indicate the corresponding voltage level of displacement for each color used.

Figure 3:
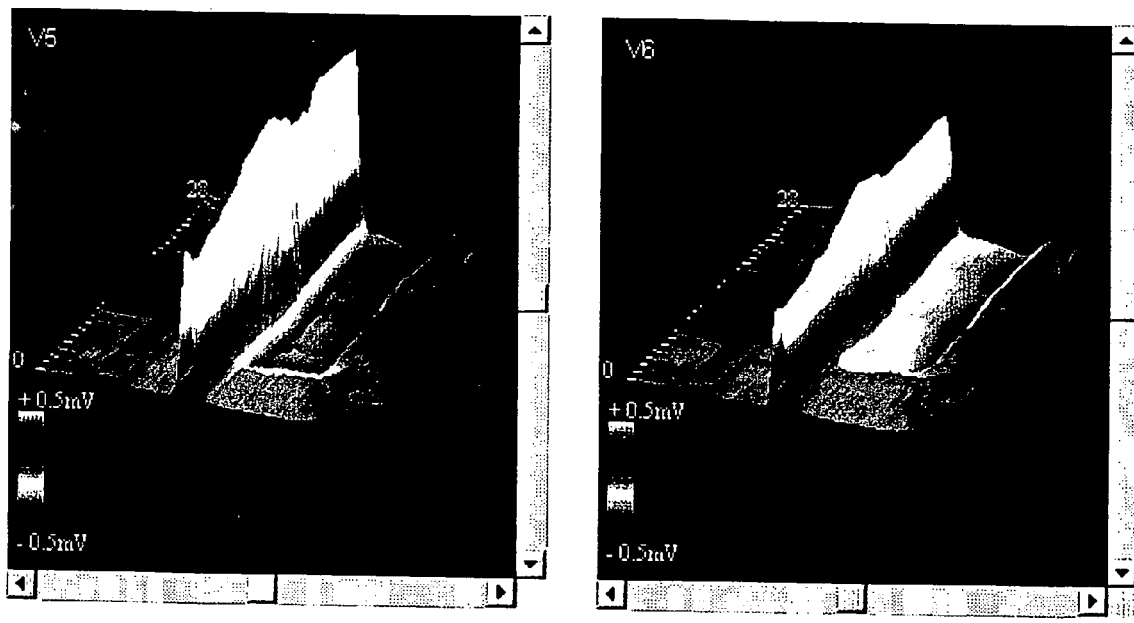
FIGS. 3(a) and 3(b) are two color illustrations showing three dimensional representations of physiological patient data from a cyclic physiological waveform according to the invention.
Figure 4:
FIGS. 4–7 are examples of rotated or animation views of the three dimensional representations according to the invention.
Figure 5:
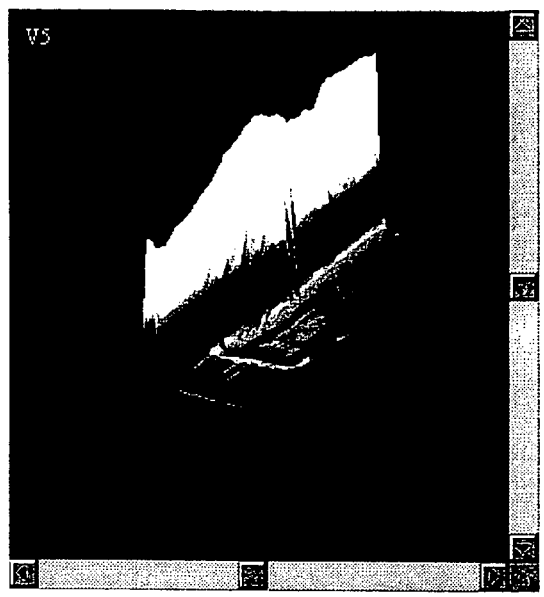
Figure 6:
Figure 7:

As shown in FIG. 3, the successive waveforms are plotted in a stacked colorized representation to provide a perspective or representative three dimensional view of the physiological patient data over an extended period of time. This presentation highlights subtle trends that may exist in the data, but are difficult to observe with ordinary display presentations. In a preferred form of the invention, the representative three dimensional view of the data can be rotated by the processor so that it can be viewed on the display by the user from different perspectives. The use of color to enhance this display allows easy detection by the clinician of significant aspects of the data, for example, the yellow and orange portions of the data displayed in FIG. 3 indicate a significant S-T depression in the ECG data.

FIGS. 4–7 illustrate how the representative three dimensional view of the data can be rotated by the processor so that it can be viewed on the display by the user from different perspectives. Essentially, the processor rotates the representative three dimensional image by rotating the X, Y, and Z axes. As the image rotates, the operator is able to more easily characterize different segments of the median waveforms. For example, when using median ECG waveforms, the operator may be able to more easily characterize the difference in amplitudes of the median waveforms using a view similar to FIG. 7. The operator may rotate the image a full 360 degrees in order to view each side of the image.

Various other features and advantages of the invention are set forth in the following claims.

What is claimed is:

1. A method of displaying physiological patient data from a cyclic physiological waveform, the method comprising the steps of:
   acquiring physiological patient data from a cyclic physiological waveform;
   storing the physiological patient data in a memory array;
   displaying the physiological patient data in a three-dimensional representation by parsing the physiological patient data into a series of waveforms such that each successive waveform is plotted in a temporal alignment to allow detection of long term trends in the physiological patient data;
   colorizing the three-dimensional representation by automatically selecting a first data point along a current waveform in the series of waveforms, the selected first data point having a representative X coordinate, Y coordinate and Z coordinate,
   automatically identifying a first area between the current waveform and a second waveform in the series of waveforms based upon the coordinates of the selected first data point,
   automatically applying a first predetermined color to the identified first area if the amplitude of the selected first data point is in a first range,
   automatically applying a second predetermined color to the identified first area if the amplitude of the selected first data point is in a second range, and
   automatically applying a third predetermined color to the identified first area if the amplitude of the selected first data point is in a third range.

2. The method of claim 1, wherein the area is a triangle formed between the first data point along the current waveform, a second data point along the current waveform having a different X coordinate value than the first data point, and a third data point along the second waveform having the same X coordinate value as the second data point along the current waveform.

3. The method of claim 1, wherein the area is a triangle formed between the first data point along the current waveform, a second data point along the second waveform having a different X-coordinate value than the data point, and a third data point along the second waveform having the same X-coordinate value as the first data point along the current waveform.

4. The method of claim 1 further comprising the step of selecting a second data point along the current waveform in the series of waveforms, the second data point having a representative X coordinate, Y coordinate and Z coordinate, identifying an area between the current waveform and the second waveform based upon the coordinates of the selected second data point, and applying a predetermined color to the area based on the amplitude of the selected second data point.

5. The method of claim 1, wherein the predetermined color is applied based upon whether the amplitude of the selected first data point is within a predetermined range.

6. The method of claim 5, wherein the predetermined range is +0.5 mV to −0.5 mV.

7. The method of claim 1, wherein each waveform is a median waveform, and wherein each median waveform represents a plurality of cycles of the cyclic physiological waveform.

8. The method of claim 1, wherein the physiological patient data is electrocardiogram data.

9. The method of claim 1, wherein the physiological patient data is blood pressure data.

10. The method of claim 1, wherein the physiological patient data is cardiac output data.

11. The method of claim 1, wherein the physiological patient data is pulse oximetry data.

12. An apparatus for displaying physiological patient data from a cyclic physiological waveform, the apparatus comprising:
   a display for displaying physiological patient data from a cyclic physiological waveform in a three-dimensional representation by parsing the physiological data into a series of waveforms such that each successive waveform is plotted in a temporal alignment to allow detection of long term trends in physiological data;
   a processor capable of colorizing the three-dimensional representation by automatically selecting a first data point along a current waveform in the series of waveforms, the selected first data point having a representative X coordinate, Y coordinate and Z coordinate,
   automatically identifying a first area between the current waveform and a second waveform in the series of waveforms based upon the coordinates of the selected first data point,
   automatically applying a first predetermined color to the identified first area if the amplitude of the selected first data point is in a first range,
   automatically applying a second predetermined color to the identified first area if the amplitude of the selected first data point is in a second range, and
   automatically applying a third predetermined color to the identified first area if the amplitude of the selected first data point is in a third range.

13. The apparatus of claim 12, further comprising a patient monitoring device providing the physiological patient data.

14. The apparatus of claim 13, wherein the patient monitoring device comprises a transducer for acquiring the physiological patient data from a patient.

15. The apparatus of claim 13, wherein the patient monitoring device is a Holter monitor.

16. The apparatus of claim 13, wherein the patient monitoring device is a stress-testing monitor.

17. The apparatus of claim 12, further comprising a memory device connected to the processor.

18. The apparatus of claim 17, wherein the physiological patient data is stored in a memory array.

19. The apparatus of claim 12, wherein the display is a black and white display capable of displaying shades of gray in between black and white.

20. The apparatus of claim 12, wherein the display is a red-blue-green color display.

21. The apparatus of claim 12, wherein the processor further comprises software for animation and walk through of three-dimensional representations.

22. The apparatus of claim 12, wherein the processor further comprises software to receive the physiological data.

23. The apparatus of claim 12, wherein the processor further comprises software to parse the physiological patient data.

* * * * *